US010376691B2

United States Patent
De Toni et al.

(10) Patent No.: US 10,376,691 B2
(45) Date of Patent: Aug. 13, 2019

(54) ELECTRODE SYSTEM, DEVICE AND METHOD FOR THE TREATMENT OF EYE DISEASES, IN PARTICULAR DRY EYE

(71) Applicant: RESONO OPHTHALMIC S.R.L., Trieste (TS) (IT)

(72) Inventors: Alessandro De Toni, Padua (IT); Alessandro Pozzato, Vicenza (IT); Gianantonio Pozzato, Vicenza (IT); Alfredo Ruggeri, Padua (IT); Matteo Scaramuzza, Chirignago (IT); Antonio Trani, Dueville (IT)

(73) Assignee: SML MASCHINENGESELLSCHAFT M.B.H., Lenzing (AT)

( * ) Notice: Subject to any disclaimer, the term of this patent is extended or adjusted under 35 U.S.C. 154(b) by 0 days.

(21) Appl. No.: 15/540,721

(22) PCT Filed: Oct. 27, 2016

(86) PCT No.: PCT/IB2016/001541
§ 371 (c)(1),
(2) Date: Jun. 29, 2017

(87) PCT Pub. No.: WO2017/072575
PCT Pub. Date: May 4, 2017

(65) Prior Publication Data
US 2017/0354818 A1    Dec. 14, 2017

(30) Foreign Application Priority Data
Oct. 29, 2015  (IT) ............................ 102015000066819

(51) Int. Cl.
*A61N 1/06* (2006.01)
*A61N 1/36* (2006.01)
*A61N 1/04* (2006.01)

(52) U.S. Cl.
CPC ............. *A61N 1/06* (2013.01); *A61N 1/0484* (2013.01); *A61N 1/36046* (2013.01)

(58) Field of Classification Search
CPC ..... A61N 1/06; A61N 1/0543; A61N 1/36046
See application file for complete search history.

(56) References Cited

U.S. PATENT DOCUMENTS 7,300,437 B2    11/2007  Pozzato
7,571,003 B2    8/2009   Pozzato
(Continued)

FOREIGN PATENT DOCUMENTS

CN      203408044 U     1/2014
EP      1467687 B1      10/2004
(Continued)

OTHER PUBLICATIONS

Lemp Ma. Report of the National Eye Institute/Industry workshop on clinical trials in Dry Eyes. Clao J. 1995;21:221-232.
(Continued)

*Primary Examiner* — Eric D. Bertram
(74) *Attorney, Agent, or Firm* — Lucas & Mercanti, LLP; Klaus P. Stoffel

(57) ABSTRACT

An electrode system for treating dry eye, including at least one electrode having a portion intended to be applied in contact with the eye, the eye orbit, the temple, the eyelid areas or a part of them that respectively imitates the shape of the eye surface, the eye orbit, the temple, the eyelid areas or a part of them or wherein the portion of the intended to be applied in contact with the eye, the eye orbit, the temple, the eyelid areas or a part of them has a flexible and adaptable shape so that a form-fit is achievable between the portion of the electrode and the surface shape of the eye, the eye orbit, the temple, the eyelid areas or a part of them. The portion of the electrode is fed with an electromagnetic wave of dis-
(Continued)

torted sinusoidal current with a resonance frequency which includes the related harmonics.

7 Claims, 11 Drawing Sheets

(56) References Cited

U.S. PATENT DOCUMENTS

| | | | |
|---|---|---|---|
| 7,713,267 | B2 | 5/2010 | Pozzato |
| 8,457,751 | B2 | 6/2013 | Pozzato |
| 8,918,181 | B2 | 12/2014 | Ackermann et al. |
| 2006/0211934 | A1 | 9/2006 | Hassonjee et al. |
| 2008/0177352 | A1 | 7/2008 | Pascual-Leone et al. |
| 2010/0010481 | A1* | 1/2010 | Pozzato ............. A61B 17/3211 606/9 |
| 2011/0081333 | A1* | 4/2011 | Shantha ................. A61N 1/328 424/94.62 |
| 2013/0066396 | A1 | 3/2013 | Gekeler et al. |
| 2013/0172829 | A1* | 7/2013 | Badawi ................. A61F 9/0008 604/294 |

FOREIGN PATENT DOCUMENTS

| | | |
|---|---|---|
| EP | 1631203 B1 | 8/2009 |
| EP | 1545699 B1 | 10/2009 |
| EP | 1633263 B1 | 8/2010 |
| WO | 2012114066 A1 | 8/2012 |
| WO | 2012139063 A2 | 10/2012 |
| WO | 2014119025 A1 | 8/2014 |

OTHER PUBLICATIONS

Report of the International Dry Eye WorkShop (DEWS), Ocul Surf. 2007;5(2):69-204.

Dal Maschio M et al. Biophysical effects of high frequency Electrical field (4-64 MHz) on muscle fibers in culture. Basic Applied Myology. 2009;19 (1):49-56.

B. Kronemyer. Resonax emits high frequency currents to stimulate tissues. Aesthetic Buyers Guide. Sep.-Oct. 2006. www.miinews.com . . . .

Schiffman RM et al. Reliability and validity of the eye Surface Index. Arch Ophthalmol. 2000;118:615-621.

Suzuki M et al. Tear osmolarity as biomarker for dry eye disease severity. Invest Ophthalmol Vis Sci. 2010;51:4557-4561.

* cited by examiner

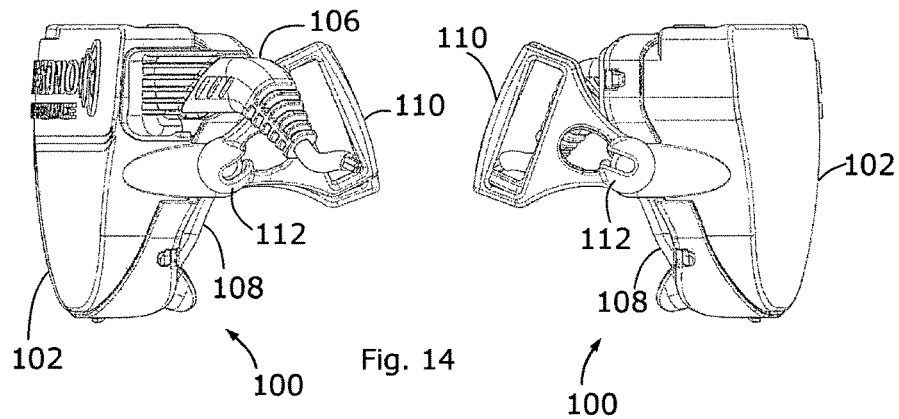
Fig. 14
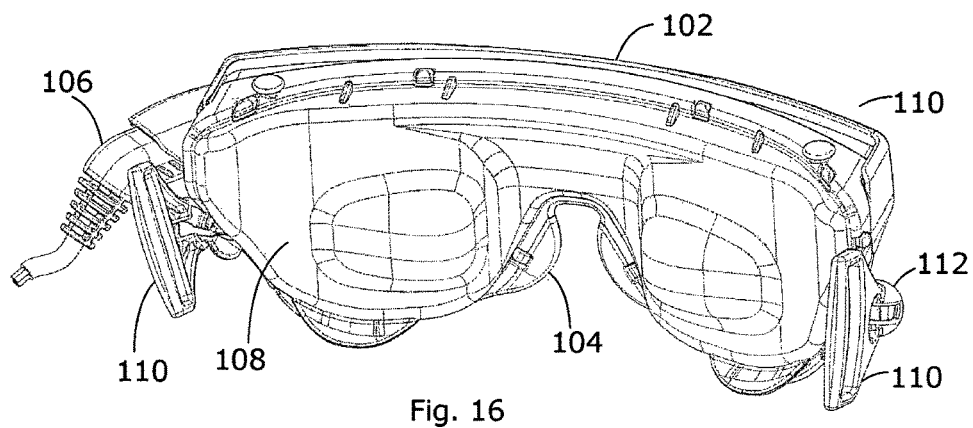
Fig. 15
Fig. 16

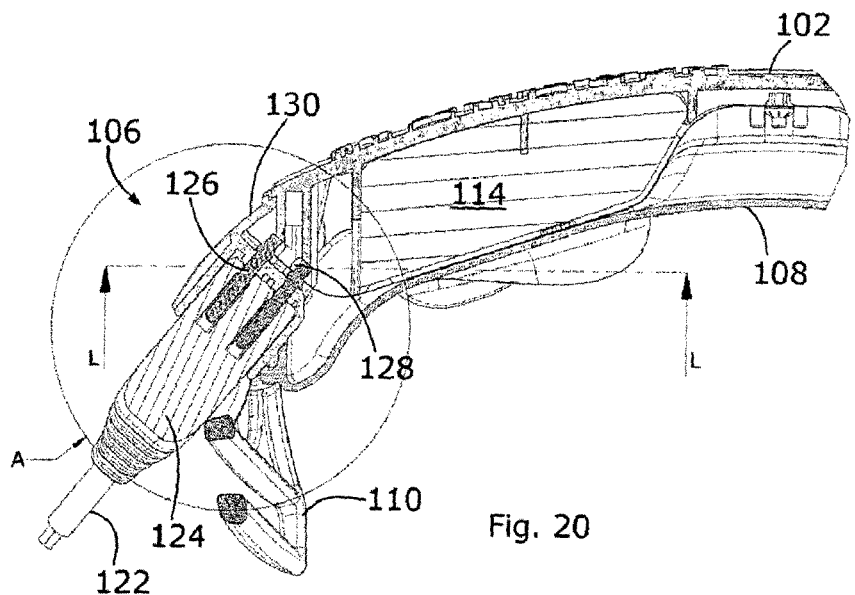
Fig. 20
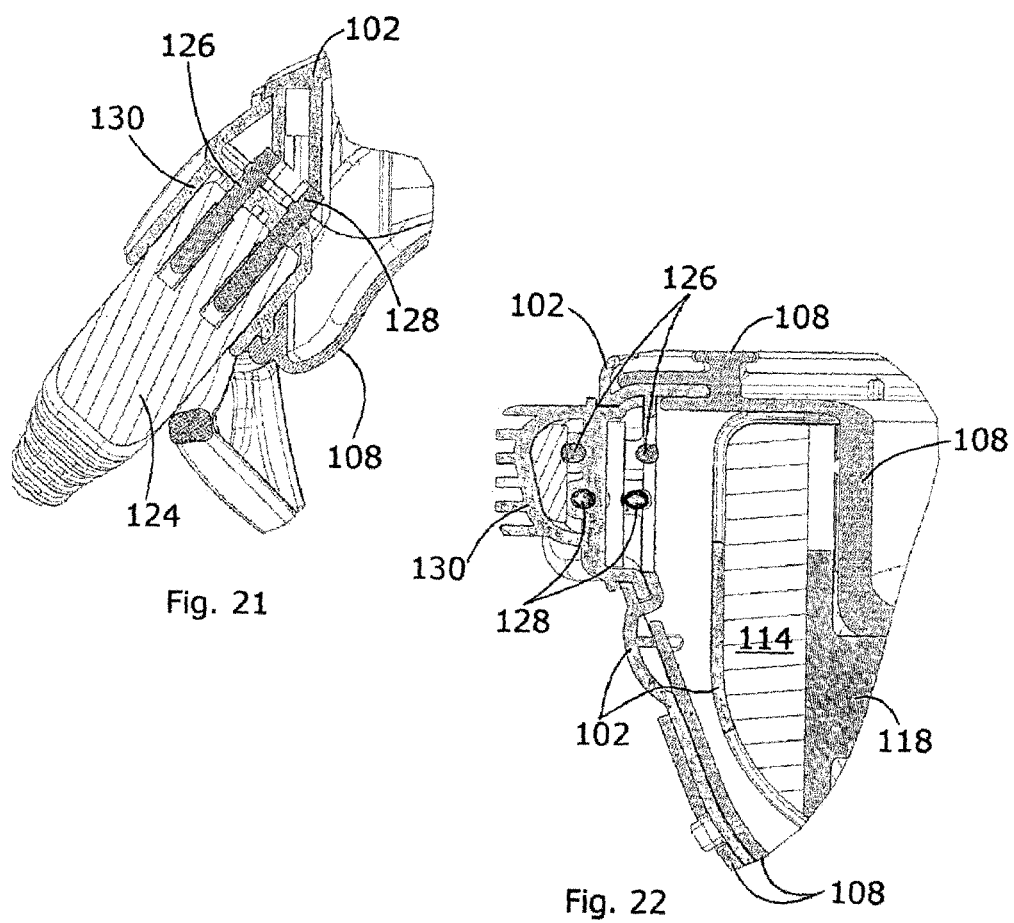
Fig. 21
Fig. 22

ELECTRODE SYSTEM, DEVICE AND METHOD FOR THE TREATMENT OF EYE DISEASES, IN PARTICULAR DRY EYE

The present application is a 371 of International application PCT/IB2016/001541, flied Oct. 27, 2016, which claims priority of IT 10 2015 000 066 819, filed Oct. 29, 2015, the priority of these applications is hereby claimed and these applications are incorporated herein by reference.

BACKGROUND OF THE INVENTION

The invention relates to an electrode system, a respective device and method for the treatment of eye diseases, in particular dry eye, in which an adaptability of the electrode to the shape of the body area to be treated is provided.

STATE OF THE ART

The guidelines of the American National Eye Institute on clinical trials in dry eye disease[1] had defined dry eye as a "disorder of the tear film due to insufficient tear production or excessive tear evaporation, with the deterioration of the inter-eyelid eye surface and symptoms of eye discomfort". More recently, the term "tear dysfunction" (Dysfunctional Tear Syndrome, DTS)[2] is preferred to "dry eye"; the former clinically frames a multifactorial disease of the tears and eye surface that produces symptoms of discomfort, visual disturbance and tear film instability, associated with increased osmolarity of the tear film and inflammation of the eye surface. DTS is a disorder commonly seen in ophthalmology practice and, at varying degrees of severity, affects roughly 20% of adults over 40 years of age.

The origin of the disease is linked to pathological conditions of one or more portions of the functional unit that includes the tear film, the eye surface (cornea, conjunctiva, accessory lacrimal glands, meibomian glands), the mucoepidermal junction, the main lacrimal gland and nervous connection systems, excretory ducts and the nasolacrimal sac.

The symptoms can manifest as mild discomfort or burning at varying intensity, foreign body sensation, dryness, photophobia. In severe cases, the disease can progress to affect the corneal tissue and determine ulcers, infiltrates, visual disturbances.

DTS therapy, only symptomatic, has the aim to maintain an adequate lubrication of the eye surface and is substantially based on the use of tear substitutes (whose frequency of administration during the day in the most serious cases can be up to tens of times), gels or ointments during the night, and topical anti-inflammatory drugs.

A symptomatic therapy is, for example, the application of "heated moisture" in connection with pulsed air under pressure as described in patent documents WO 2012/114066 A1 and EP 1 467 687 B1. Other symptomatic treatments include a combination of localized heat and intermittent pressure.

Another dry eye treatment strategy known in the art proposes electrical nerve stimulation of the lacrimal gland through electrodes which are implanted. Therefore, this is an invasive method. Electrodes for such a therapy are described in WO 2012/139063 A2 and U.S. Pat. No. 8,918,181 B2. A nasal neurostimulation device is also known, wherein a device is inserted into the mucous membrane of the nasal cavity and another is inserted in subcutaneous form below the eyebrow to increase tear production. Dry eye treatment with pulsed light is also known. US documents US 2011/081333 A1 and US 2013/172829 A1 propose, in a very general form, dry eye treatment with electrostimulation at various frequencies. The electrodes proposed in the two documents are not yet ideal to ensure a uniform distribution of the electromagnetic waves in a simple way.

All these above-mentioned therapies are symptomatic and do not cure the disease. Repetition of applications is therefore necessary.

SUMMARY OF THE INVENTION

The object of the invention is to propose a method and related devices used in dry eye therapy which overcome the aforesaid disadvantages and that not only treat the symptoms but eliminate the origin (hypo-secretion or hyper-evaporation in the case of dry eye) of the disease or at least reduce the frequency of symptomatic treatments.

The above-mentioned objects, other objects and advantages which will be better apparent hereinafter are achieved by an electrode system as defined by the first claim, and specifically by an electrode system for treating dry eye, which comprises one or more electrodes wherein (a) a portion of said one or more electrodes intended to be applied in contact with the eye, the eye orbit, the temple, the eyelid areas or a part of them respectively imitates the surface shape of the eye, the eye orbit, the temple, the eyelid areas or a part of them or wherein (b) a portion of said one or more electrodes intended to be applied in contact with the eye, the eye orbit, the temple, the eyelid areas or a part of them is flexible and adaptable in its shape in such a way that in the cases (a) and (b) a form-fit is achievable between said portion of said one or more electrodes and the surface shape of the eye, the eye orbit, the temple, the eyelid areas or a part of them, wherein the portion of said one or more electrodes intended to be applied in contact with the eye, the eye orbit, the temple, the eyelid areas or a part of them is fed or feedable with an electromagnetic wave of distorted sinusoidal current with a resonance frequency, preferably a 4 MHz resonance frequency, which includes the related harmonics, preferably at least the second and the third harmonic; in a preferred variant of the invention, the electromagnetic wave of distorted sinusoidal current includes harmonics up to 64 MHz.

Advantageously, said portion of said one or more electrodes is flexible and adaptable in its form and comprises, in a sandwich structure, in the following order: a damping cushion, a conductive and radiating element and an insulation layer.

The geometric adaptability of the electrode, i.e. the fact that said portion of said one or more electrodes and the surface shape of the eye, the eye orbit, the temple, the eyelid areas or a part of them are form-fit coupled, allows a uniform transmission of the electromagnetic waves on the relevant parts of the body thus avoiding also overheating or electromagnetic waves concentrations in individual points of the application area. With such an electrode structure, it is possible to apply—in a simple and non-invasive way—electromagnetic waves on entire or partial surface areas of the eye, the eye orbit, the temple and the eyelid areas.

An essential part of the electrode is therefore the fact that the electrode portion in contact with the treatment area corresponds in its shape to the relative shape of the area to be treated to ensure a uniform transmission, extended over the entire area to be treated. Another important part of the electrode system is the fact that it is fed/feedable with electromagnetic waves as defined in the first claim, waves that—as will be seen later on—allow great progress in treating dry eye. The electrode system according to the invention is also suitable to treat other eye diseases.

Advantageously, the electrodes may cover the entire eye area of the eyelid, or, in another variant, only a part of it. In other advantageous variants of the invention, the system can include four electrodes which are preferably supported on the temporal and eyelid areas of the eye. Other variants include two electrodes applied on the two areas of the patient's eyelid. The number of electrodes within the system and the electrode dimensions are chosen according to the areas to be treated.

Advantageously, the electrode can be in the form of a sheet, that is, with the third dimension much smaller than the other two dimensions.

In preferred variants of the invention, said portion of said one or more electrodes is flexible and adaptable in its shape and is chosen from: a flexible metallized substrate; a polymer, preferably a silicone rubber, comprising metal particles and/or wires; a metallized fabric; a metallic fabric; and combinations of these. Particularly preferred is the metallic fabric, such as for example aluminum or silver fabrics. Preferably, the polymer is soft and inert. Advantageously, the polymer is a silicone rubber. Preferably, the polymer has conductive nanoparticles, in particular metallic nanoparticles, embedded within. It is therefore a blend of a soft and inert polymer and metal nanoparticles in an appropriate concentration. Any other polymer modifications suitable to make it electrically conductive to the stimulation frequencies are acceptable, thus also the integration of wires. The versions with a metallized substrate are less preferred because the metallization often makes the material too rigid.

In a particularly preferred embodiment of the invention, the portion of said one or more electrodes is flexible and adaptable in its shape and includes as a conductive and radiating element and a metallic fabric which has different extensibility in the two dimensions that define its surface extension. The conductive and radiating element serves to transmit the electromagnetic waves. A different extensibility in the two dimensions that define its superficial extension allow uniform adaptation to the shape of the eye area to be treated. For treatments of the eyelid area in the closed state of the eye, particularly suitable is a material which, in the direction that during use of the system corresponds to the line on which the eyes are, is extendable to about 100%, while in the orthogonal direction (i.e., along the line that corresponds to the extension of the nose) with respect to this is extensible to 65%, taking into account the eyelid size of the average patient. Conductive fabrics are known in the market and are, for example, marketed as electric field screens; a supplier with a wide choice is, for example, Less EMF Inc., Latham N.Y. 12110, USA.

In an advantageous embodiment of the invention, the electrode system further comprises a thermal probe. With the thermal probe is possible to determine the temperature of the system in contact with the eye. The temperature should preferably not exceed 40° C. Advantageously, a system for interrupting the electrode system powering in the event of too high temperatures may also be provided. In an embodiment of the invention, the temperature probe can be integrated in the electrode portion in contact with the area to be treated or in proximity to this. Advantageously, the electrode comprises a device for impedance detection.

In a further, particularly preferred embodiment of the invention, the portion of said one or more electrodes is flexible and adaptable in its shape and comprises, on the side intended to come into contact with the patient, a layer of insulation suitable to allow frequencies above 100 kHz to pass, advantageously blocking frequencies below 100 kHz. The insulating layer therefore acts as a filter and is suitable to protect the patient from low frequencies, but allows high frequencies to pass, in particular the desired harmonics. Suitable materials for the isolation layer are, for example, silicone rubbers, polyurethanes (PU), thermoplastic elastomers (TPE), such as, for example, the product ProvaMed TPE 1140 by ACTEGA, which is already certified in the medical field.

Another embodiment of the invention provides that the electrode system according to the invention also includes one or more cushions with gel or similar placed at least partially directly or indirectly in contact with said portion of said one or more electrodes. The cushion allows to improve the adhesion of the electrode to the respective area to be treated, such as, for example, the eyelid, and this in a simple, effective way and with minimal discomfort for the patient. For example, also cushions filled with liquids or soft deformable materials, such as foam rubber, also with "memory" effect, are conceivable. These damping cushions help to deform the electrode parts which then adapt to the shape of the area to be treated and at the same time ensure a soft contact with the eye.

In variants of the invention, the electrode may be covered on at least one side, for example on the side that comes into contact with the area to be treated, with a protective layer, such as for example cotton. Also between the gel cushion and the electrode, i.e. the electrode conductive part, a protective layer may be provided. A possible structure inside the electrode system according to the invention can have the following succession: protective layer, electrode (i.e. conductive part of the electrode), protective layer, gel cushion.

The protective layers are not strictly necessary since the operational hypothesis of the device according to the invention is the capacitive charge transfer at high frequency, but ergonomic conditions and biocompatibility can be improved for certain types of electrodes (in particular for electrodes that operate producing heat). The electrode can also have direct contact with the eye, the eye orbit, the temple, the eyelid areas. Increased safety is instead provided by the above-mentioned insulation layer, which allows to exclude low frequency transmission and limit with great safety the operation of the system to the high-frequency capacitive charge transfer.

Advantageously, the material chosen for the electrode is not subject to excessive heat generation during operation, to not generate temperatures over 40° C. on the areas to be treated.

Favourite currents applied on the eye, the eye orbit, the temple, the eyelid areas correspond, for instance, to surface powers of about 30-100 ml/cm$^2$/s, more preferably of 60-100 mJ/cm$^2$/s; a particularly preferred value is about 80 mJ/cm$^2$/s.

In a particularly preferred embodiment of the invention, the portion of said one or more electrodes is flexible and adaptable in its form and comprises, in a sandwich structure, in the following order: a damping cushion, a conductive and radiating element and an insulation layer wherein the conductive and radiating element is integrated as a window in an opening of a film which carries an electrical circuit to feed the conductive and radiating element with electromagnetic waves, wherein the film is part of the electrode and wherein the damping cushion, the conductive and radiating element, the insulation layer and the film are all flexible and adaptable in their shape to the eye, eye orbit, temple and eyelid areas or a part of them.

Advantageously, the electrode system according to the invention comprises an electric circuit for the transmission of electromagnetic waves configured such that the electrical circuit is open and that is closable only by an external object as a load impedance to which electromagnetic waves are transmitted. The electrode system according to the invention comprises an electric circuit for the transmission of electromagnetic waves configured in such a way that the part of the patient's body destined to the treatment becomes part of the circuit and without which the passage of the electromagnetic wave is not possible. In other words, the electrical circuit without the surface to be treated is an open circuit. Its operation does not exploit the passage of current inside it to heat the electrode through Joule effect, but sees the patient's body or the external object as a load impedance to which electromagnetic waves are transmitted. With his general knowledge, the expert easily realizes such a circuit.

In a particularly preferred embodiment of the invention, the electrode system is a mask or a pair of goggles in which the portion of said one or more electrodes extends across the entire area of the mask or the goggles that is destined to cover the eye, the eye orbit, the temporal areas and/or the eyelid areas of the eye or part of them, particularly the portion in its extension can involve most of the meibomian glands and of the lacrimal glands. Such a structure is easily fixable on the head and can comfortably cover the areas to be treated with the electrode.

In a very advantageous variant of the invention, said portion of said one or more electrodes is suitable to cover with form-fit coupling the eyelids in their closed state.

The above-described embodiments for the electrode system, in particular also the ones defined in claims 2 to 6, can also be realized regardless of the form of electromagnetic waves that feed the electrode; these measures are useful also for other types of treatment, as features highlighted in the claims from 3 to 5 can also be implemented in electrodes not adaptable in their shape.

A further aspect of the invention relates to an electrostimulation device for treating dry eye, comprising an electrode system according to the invention and a radio frequency circuit suitable to emit an electromagnetic wave of distorted sinusoidal current with a resonance frequency which includes the related harmonics, preferably at least the second and the third harmonic, in which the electromagnetic wave of distorted sinusoidal current feeds said one or more electrodes, and in particular said portion of said one or more electrodes intended to be applied in contact with the eye, the eye orbit, the temple, the eyelid areas or a part of them.

Advantageously, the wave has a frequency of 4 MHz. Very preferably, with very satisfactory results in the treatment of eye pathologies, especially of dry eye, the resonance frequency amounts to 4 MHz. In a preferred embodiment, the electromagnetic wave of distorted sinusoidal current has a 4 MHz resonance frequency and includes harmonics up to 64 MHz.

The radiofrequency circuit belonging to the device according to the invention is therefore a broadband circuit. Such a circuit is intended to allow the passage of harmonics. Their significant presence in the above mentioned electromagnetic wave is desired. The random presence of harmonics in narrow band filters, designed to pass a single frequency, is not sufficient to implement the invention. Preferably, the second and the third harmonic exceed 10% of intensity in terms of amplitude in the relationship with the fundamental frequency in a load impedance range that varies from 10Ω to 2000Ω. These intensities can also be reached outside the indicated range. In the documents EP 1 545 699, EP 1 633 263 and EP 1 631 203, the radiofrequency circuit comprises a resonant circuit which oscillates at the respective resonant frequency and that is realized with a merit factor or Q factor that allows the passage of harmonics of the resonance frequency of the resonant circuit and which gives the circuit the characteristic of being a broadband circuit, a classic way to create a broadband circuit. The electromagnetic wave with such a resonance frequency transmitted to the tissue to be treated then puts the tissue, i.e. the relevant molecules in oscillation or resonance at their respective resonance frequency.

The casual, unexpected and surprising observation of the increase in the amount of tears in subjects without a clinical diagnosis of DTS following a cosmetic anti-wrinkle treatment by electrostimulation with a device similar to the device according to the invention (as described in European patent EP 1 545 699 B1), but with a different electrode, has allowed to hypothesize that the electrostimulation of the periorbital skin surface benefits the lacrimal function.

Low-intensity and high frequency electrostimulation used by the device according to the invention is based on the principle of the Quantum Molecular Resonance (RQM) i.e. of the possibility of transferring energy to the biological tissues in the form of oscillating electric fields. A study of a model of muscle fibres in culture[3] performed at the Department of Human Anatomy and Physiology of the University of Padua highlighted that the energy in RQM determines the change in the membrane potential and increase in intracellular free calcium. The effects of electric fields in RQM are so closely related with the cellular biochemistry and with the activation of intracellular metabolic pathways and find therapeutic application in Physiotherapy and Cosmetic Medicine, conditions in which it is useful to stimulate cell metabolism and promote tissue regeneration.[4]

A clinical preliminary study of seven patients with moderate to severe DTS and blepharitis showed the clinical and subjective improvement in 60% of patients undergoing electrostimulation and maintenance of clinical outcome after three months after the end of treatment.

In the case of DTS, it can be assumed that the high-frequency of the electric field can stimulate the lacrimal system by reactivating the activities of the glandular tissue, stimulating the meibomian and the lacrimal glands, with functional benefits to the surrounding tissues as well. The mild hyperthermia generated by the electrical flow and a possible massage exerted by the operator on the periorbital region could also help to reactivate the physiological tear and lipid secretion and therefore not only act on the symptoms of the disease.

The induction of a greater quantity of natural tears following the application of RQM therefore leads to a qualitative and quantitative physiological balance of the lacrimal film with relevant positive results from the clinical and subjective point of view.

Patent documents EP 1 545 699 B1, EP 1 633 263 B1 and EP 1 631 203 B1, as well as the corresponding U.S. Pat. No. 7,300,437 B2, filed on Dec. 2, 2005, U.S. Pat. No. 7,571,003 B2, filed on Jan. 6, 2005, U.S. Pat. No. 7,713,267 B2 filed on Feb. 18, 2005 and U.S. Pat. No. 8,457,751 B2, filed on Jun. 22, 2009, which are fully incorporated herein by reference, describe devices for wrinkle treatment and blood clotting and lancets that include components, such as the radiofrequency circuit, to create distorted sinusoidal high-frequency electromagnetic waves which can be used in the electrode system, in the device and in the method and use according to the invention. None of the documents contain an indication that such waves could be useful in the treatment of eye diseases, especially of DTS.

A further aspect of the invention relates to a method for treating dry eye, which comprises the application of an electromagnetic wave of distorted sinusoidal current with a resonance frequency, preferably with a resonance frequency of 4 MHz, and comprising the related harmonics, preferably at least the second and the third harmonic and still more preferably, in the case of a 4 MHz resonance frequency, harmonics up to 64 MHz, on the eye, the eye orbit, the temple, the eyelid areas or on a part of them. The application can take place, simultaneously or in succession, on several of the areas defined above. As described above and as evident from the clinical study described later, the proposed method significantly reduces the symptoms of dry eye and eliminates them in some patients, at least for a period of time that exceeds several months. In some cases, the origin of the pathology seems to be removed, in others the time needed between treatments in order to treat symptoms manifested after the last treatment is prolonged.

The method can also be implemented with standard electrodes known in the prior art which, however, are unlikely to cover by form-fit coupling the areas to be treated.

Preferably, the application according to the method of the invention is carried out by the electrode system according to the invention or by the electrostimulation device according to the invention.

In a preferred embodiment, the electromagnetic wave as defined above is applied over the entire surface of the closed eyelid. In a preferred embodiment, the electromagnetic wave as defined above is applied over the entire closed upper eyelid. The use of electrodes according to the invention that advantageously cover the entire eyelid area and adhere well to the eyelid gives better results than electrodes that cover other areas of the eye or of its socket.

In an embodiment of the method according to the invention, the treatment takes place in two phases, where in the first phase the electrodes, preferably four, are applied on the temporal areas and externally to the lower eyelid surfaces of both eyes, and where the subsequent second phase, electrostimulation is made by means of a handpiece electrode that performs an "8" movement following the orbital bone conformation. Advantageously, in the first phase, electrodes are activated for a certain duration, for example one minute each, and the cycle is repeated 4 times for an electrostimulation of the total duration of 16 minutes. Preferably, in the second phase, the handpiece is activated for about ten minutes, or for example for two 3-minute cycles, for a total of six minutes. Advantageously, for example, 12 sessions are applied, composed by these two phases, distributed in eight weeks, two sessions per week in the first four weeks and one session per week in the following four weeks.

In a preferred embodiment, the electrode system according to the invention comprises more electrodes that can be activated sequentially or simultaneously.

A last aspect of the invention concerns the use of the electrode system, the device and of the method according to the invention for the treatment of ophthalmic diseases related to the cornea, such as for example blepharitis or epithelial wounds, and/or to the retina, such as for example, retinitis pigmentosa or age-related degenerative maculopathy.

Clinical evidence in the application of the invention also on other eye diseases has shown promising results. The electrode system and the device according to the invention allow the non-invasive and uniform application of electromagnetic waves on the eye, eye orbit, in temporal and eyelid areas and parts of them, thus opening the possibility of treating any eye pathology that is sensitive to such treatment.

The treatment of age-related macular degeneration and retinitis pigmentosa with electrostimulation is known in the art (US 2013/0066396 A1), which, however, proposes electrodes having a shape that does not adhere to the shape of the eye, the eye orbit, the temple or the eyelid areas and does not use the particular sinusoidal waves identified for the invention.

All the characteristics indicated above for a single aspect (electrode system, device, method, use) according to the invention can be transferred, mutatis mutandis, to other aspects of the invention. The above objects and advantages will be better highlighted during the description of preferred examples of the invention, given by way of example and not of limitation.

Variants of the invention are the object of the dependent claims. The description of preferred examples of the invention is given by way of example and not of limitation.

BRIEF DESCRIPTION OF THE DRAWINGS

FIG. 14 shows the electrode system of FIG. 11 in two side views;

FIG. 15 shows the electrode system of FIG. 11 in a semi-frontal perspective view;

FIG. 16 shows the electrode system of FIG. 11 in a rear perspective view;

FIG. 20 shows the section G-G according to FIG. 17;

FIG. 21 shows the detail A of FIG. 20;

FIG. 22 shows the section L-L according to FIG. 20;

DETAILED DESCRIPTION OF THE INVENTION

Figure 1:
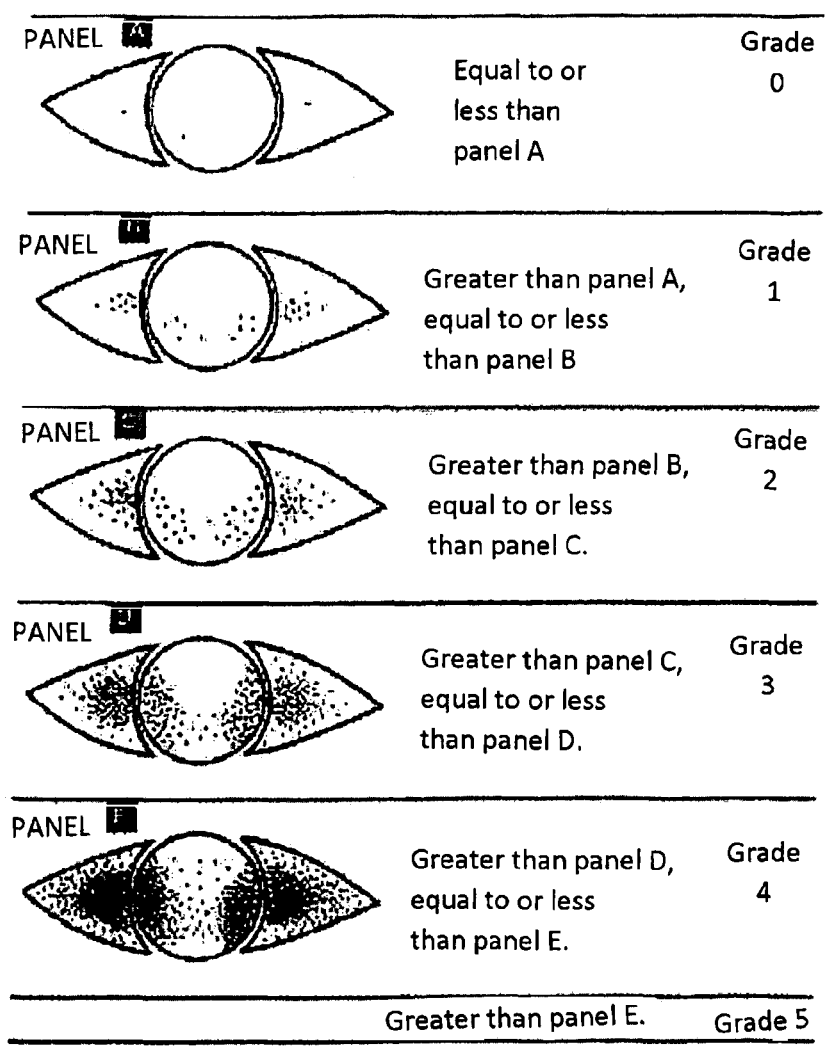
FIG. 1 represents the Oxford scheme for the evaluation of eye surface staining (In: Report of the International Dry Eye WorkShop (DEWS), Ocul Surf. 2007; 5(2):69-204)

A study is aimed to evaluate the effects of electrostimulation carried through the periorbital skin surface using the medical device according to the invention on the symptoms, clinical objectivity and quality of the tears of patients with DTS. These effects have been measured with respect to the variation of the value of the following parameters at the end of treatment compared to pre-treatment condition (baseline): (a) eye symptoms (score of the OSDI—Ocular Surface Disease Index questionnaire, Italian version, and quantity of tear substitutes used); (b) clinical condition (biomicroscopy of the eye surface, staining with fluorescein, evaluation according to the Oxford scheme); (c) quantity and quality of tear (lacrimal function tests: Schirmer-1; Tear Film Break Up Time Test (analysis of the appearance of cracks on the surface of the colored tear film tests with fluorescein); examination of tear osmolarity with TearLab™); (d) visual acuity.

The study was carried out with 27 patients with DTS that met the following criteria: (a) at least 18 years old in good general health conditions; (b) with a clinical diagnosis of DTS in both eyes; (c) time of the rupture on the surface of the tear film with fluorescein <10 seconds in both eyes; (d) Schirmer-1 test<10 mm/5 min, in both eyes; (e) osmolarity of the tear >300 m MDGs, both eyes; (f) with eye discomfort of any degree (OSDI questionnaire); (g) persons with no symblepharon winking impairment or other diseases and/or severe anatomical abnormalities of eyelids and/or eyelid occlusion. The study did not include patients that: (a) require treatment with antibiotics in eye drops; (b) are pregnant or plan to become pregnant during the study period; (c) need to start a topical or systemic anti-inflammatory treatment; (d) suffer from glaucoma and/or are being treated with hypotonic eye drops; (e) performed eye surgeries in the previous three months; (f) have suffered from eye infections in the previous 6 months, or with a history of recurring eye infections (e.g. herpes, etc.); (g) are carriers of not removable electrical devices (e.g. pacemakers, etc.); (h) have a dermatological pathologic condition in the facial region (e.g. rosacea, acne, etc.).

Since this is a pilot study, a formal number calculation is not feasible. The number of patients included in the study (27) allows to apply an exploratory statistical analysis to the results in order to obtain indications on the effects of the stimulation with the device according to the invention in patients with DTS. The electrostimulation was achieved by a device according to the invention.

For each patient, 12 treatment sessions over 8 weeks were applied: two session per week in the first 4 weeks and one session per week in the following 4 weeks. During electrostimulation, the instrument emitted an electric current of 80 ml/cm2/s of nominal power. Each treatment session consisted of two sequential stimulation phases.

In the first phase, two disposable adhesive electrodes according to the invention were applied by means of a conductive gel layer around each closed eye of the patient, one on the temple area and one to the outside of the lower eyelid surface, on cleansed skin, free from any cosmetic products. The four electrodes are activated sequentially for a duration of 1 minute each and the cycle was repeated four times, for an electrostimulation of the total duration of 16 minutes, after which the electrodes have been removed.

In the second phase, the electrostimulation was carried out by the use of a handpiece electrode. The doctor lies the handpiece covered with conductive gel on the patient's skin and, with a movement in the shape of "8" followed the orbital bone conformation. The handpiece was activated for two cycles of three minutes each, for a total of six minutes.

The treatment was performed with the patient sitting on a recliner, free of bulky clothing (jackets, coats, etc.) in contact with a conductive rubber plate positioned on the seat of the chair.

The device was installed in an environment considered appropriate, for temperature and humidity conditions. In this environment all treatment sessions provided by the protocol were performed so as to ensure constancy of operation.

During therapy, the patient felt a moderate heat, never unpleasant, as a result of the transmission of high-frequency current from the active electrode used. At the end of therapy the treated skin area appeared slightly reddened. The redness usually disappeared within half an hour, leaving no unpleasant feeling. Following each treatment session, before the dismissal of the patient, the evaluation of the anterior segment was performed for both eyes using biomicroscopy (slit lamp).

With patients with DTS recruited according to the inclusion and exclusion criteria described above base assessments were carried out.

Pre-treatment evaluations (baseline): (a) short-term and long-term medical history of DTS; (b) completion of the OSDI (Ocular Surface Disease Index) questionnaire; (c) measurement of tear osmolarity using TearLab™; (d) measurement of visual acuity (BCVA—best corrected visual acuity, corrected vision); (e) slit-lamp evaluation of the anterior segment of the eye (biomicroscopy); (f) measurement of tear secretion by Schirmer-1 test; (g) measurement of intraeye pressure; (h) measurement of corneal sensitivity; (i) measurement of the tear film stability by Break Up Time test with fluorescein (FBUT), performed three consecutive times in the case of values lower than 10 seconds; (j) evaluation of eye surface according to Oxford colorimetric pattern.

Each patient received a diary in which he/she noted a daily type and frequency of use of eye drops (artificial tears or other eye drops), the possible occurrence of adverse events (e.g. pain, photophobia, foreign body sensation, etc.), the use of drugs in other formulations. The initial study visit (Visit 1) involved a verification of the outcome parameters: (a) completion of the OSDI (Ocular Surface Disease Index) questionnaire; (b) assessing the scale of tear substitutes current usage (number of doses/day for each type of eye drops used during the week before the start of the study visit); (c) measurement of tear osmolarity using TearLab™; (d) slit-lamp evaluation of the anterior segment of the eye (biomicroscopy); (e) measurement of tear secretion by Schirmer-1 test; (f) measurement of the tear film stability by Break Up Time test with fluorescein (FBUT), performed three consecutive times in the case of values lower than 10 seconds; evaluation of eye surface according to Oxford colorimetric pattern.

Patients went to the clinic for treatment (treatment visits, visits 1-12) twice a week for the first 4 weeks and once a week for the next 4 weeks. Each visit involved checking the Diary (frequency and type of tears/other eye drops used; events or adverse reactions) and performing the biomicroscopy of both eyes.

Before the start of the eighth session of treatment, the OSDI questionnaire was compiled and measurement of tear osmolarity was performed.

A week after the end of the treatment cycle, each patient returned to the clinic for a control/final study visit (visit 13) which included the following assessments:
(a) completion of OSDI questionnaire;
(b) Diary check;
(c) measurement of tear osmolarity using TearLab™;
(d) measuring visual acuity (BCVA, corrected vision);
(e) slit-lamp evaluation of the anterior segment of the eye (biomicroscopy);
(f) measurement of tear secretion by Schirmer-1 test;
(g) measurement of intra-eye pressure;
(h) measurement of corneal sensitivity;
(i) measurement of the tear film stability by Break Up Time test with fluorescein (FBUT), performed three consecutive times in the case of values lower than 10 seconds;
(j) evaluation of eye surface according to the Oxford colorimetric pattern.

The end-of-study treatment ended the observation period.

The effectiveness of electrostimulation with the device and method according to the invention was measured with respect to the subjective evaluation of eye disorders, the clinical evaluation of the eye surface and the specific function tests. The average value of the two checks of Visit 0 and Visit 1 was used as baseline. The extent of use of eye drops has been evaluated by measuring the difference between the number of doses/day recorded by the patient on the diary in the week preceding the visit at the end of the study versus the number of doses/day reported by the patient during the week before the start of treatment (mean values).

The Ocular Surface Disease Index (OSDI) [5] is a questionnaire with 12 questions widely used in ophthalmologic practice that allows the measurement of eye irritation symptoms, caused by eye dryness, and evaluation of their impact on visual function. The 12 questions (6 related to visual function, 3 to eye symptoms, 3 to triggering exposure factors) have taken as a time reference the week before administration of the questionnaire, and for each of them there are 5 different possible answers: never, sometimes, half of the time, most of the time, all the time. The overall OSDI score ranges from 0 to 100, where 100 represents the highest possible degree of disability and, with respect to the assessment of the severity of disorders clinically carried out, the questionnaire scores have the following values (mean±SD): 9.6±14.2 in normal subjects; 20.8±20.4 in patients with mild to moderate clinical severity; 36.6±16.7 in serious subjects.
[5] The procedure was as follows: Illustrate the OSDI questionnaire to the patient and let him complete it alone. If the patient has questions, provide explanations so as not to influence the answers.

Check whether the questionnaire was filled out completely and ask the patient feedback on the answers to at least two questions to verify that it has been completed correctly and the answers correspond to the patient's current situation.

The test with fluorescein (and evaluation of the staining according to the Oxford scale), and thus the assessment of integrity of the eye surface was carried out by staining with sodium fluorescein 2%. The corneal surface and the nasal and temporal regions of the conjunctiva were evaluated individually, by means of observation with the blue filter slit lamp, and each was given a score on a scale from 0 to 5 (0 indicates the absence of fluorescence, thus of defects/faults). The procedure was as follows: Staining was evaluated following instillation of a standard volume of sodium fluorescein and observation under the slit lamp with yellow filter to reduce the excess of blue light.

The Schirmer-1 test for the measurement of the amount of tears was made by inserting into the lower fornix of the eye a sterile graduated strip of paper, for 5 minutes with closed eye. The evaluation consisted of the measurement (in millimeters) of the wetting degree along the strip of paper and the possible values ranging from 0 to 35 mm (lower scores indicate abnormality in tear production). The procedure was as follows:
1. Insert the absorbent paper over the lower lid margin, to the outer canthus, first in the right eye and then the left eye.
2. Ask the patient to close his/her eyes.
3. After 5 minutes, measure the length of the part of wet paper, excluding the folded portion.

The tear film stability was evaluated with the Tear Film Break Up Time Test with fluorescein (FBUT) instilling sodium fluorescein 2% in the lower fornix and instructing patients to blink a few times. By observation under a slit lamp with blue light and yellow filter, the time required for the formation of an area of breakage of the tear film was determined. If this time was less than 10 seconds, the test was repeated for a total of three times, followed by a calculation of the average of three observations. A FBUT value equal to or more than 10 seconds is considered normal. The procedure was as follows:
1. Instill 2 µL of sodium fluorescein 2% without preservative in the bulbar conjunctival sac of the right eye by not inducing reflex tearing (we recommend using a micropipette with a sterile tip).
2. Ask the patient to blink normally for 4-5 times without winking, and after 10-30 seconds after instillation of fluorescein, asking him to keep his eyes open and looking straight ahead.
3. Observe the 12× slit lamp and keep a constant intensity of backlight (cobalt blue light) to facilitate observation of the tear film over the entire cornea (use a yellow filter).
4. Record the time between the last blink and the development of the first dry spot or the appearance of the first dry area.
5. After observing the FBUT, run the grading according to the Oxford scheme.
6. Repeat steps 1-5 for the left eye.

The measurement of tear osmolarity was carried out with the TearLab™ test. The osmolarity of the tear is an efficient measure of DTS grade and is associated with the clinical assessment of signs and symptoms to complete gravity staging[6] The TearLab™ is a tool that allows to analyse the osmolarity of the tear in the clinic using a disposable test card. The withdrawal of the teardrop (about 50 nanoliters) is carried out in less than 2 seconds approaching the instrument to the tear meniscus that is formed in the outer area of the eyeball. The analysis is immediate and occurs automatically conveying the sample to a sensor able to test the given osmolarity value in a quantitative way. The procedure was as follows:
1. Bring the test-card to the tear meniscus to the outside canthus avoiding to stimulate the reflex tear, collect the tear sample;
2. Read the osmolarity value on the instrument display.

Table 1 summarizes the study scheme:

TABLE 1

| | Screening | Beginning of study | Beginning of treatment | Visit | | | | | | | | | | End of treatment | End of study |
|---|---|---|---|---|---|---|---|---|---|---|---|---|---|---|---|
| | 0 | 1 | 1 | 2 | 3 | 4 | 5 | 6 | 7 | 8 | 9 | 10 | 11 | 12 | 13 |
| | | | | | | Week | | | | | | | | | |
| | 0 | 1 | 1 | 1 | 2 | 2 | 3 | 3 | 4 | 4 | 5 | 6 | 7 | 8 | 9 |
| | | | | | | Day (±1) | | | | | | | | | |
| | 1 | 7 | 7 | 10 | 14 | 17 | 21 | 24 | 28 | 31 | 35 | 42 | 49 | 54 | 63 |
| Procedures | | | | | | | | | | | | | | | |
| Inclusion/exclusion | x | | | | | | | | | | | | | | |
| Informed consent | x | | | | | | | | | | | | | | |
| Diary delivery | x | | | | | | | | | | | | | | |
| Diary collection | | | | | | | | | | | | | | | x |
| Ocular clinical history | x | | | | | | | | | | | | | | |
| Use of artificial tears | | x | x | X | x | x | x | x | x | x | x | x | x | X | x |
| General clinical history | x | | | | | | | | | | | | | | |
| OSDI questionnaire | x | x | | | | | | | | | | | | | x |
| Visual acuity (BCVA) | x | | | | | | | | | | | | | | x |
| Biomicroscopy | x | x | x | X | x | x | x | x | x | x | x | x | x | X | x |
| Ocular tone | x | | | | | | | | | | | | | | x |
| Corneal sensitivity | x | | | | | | | | | | | | | | x |
| BUT test with fluorescein | x | x | | | | | | | | | | | | | x |
| Oxford assessment | x | x | | | | | | | | | | | | | x |
| Schirmer-1 test | x | x | | | | | | | | | | | | | x |
| Tear osmolarity | x | x | | | | | | | | | | | | | x |
| Safety assessment | | | x | X | x | x | x | x | x | x | x | x | x | X | x |
| Rexon-Eye treatment | | | x | X | x | x | x | x | x | x | x | x | x | X | |

During the study the use of tear substitutes was allowed. Patients could begin to use other eye drops or other drugs for topical use other than artificial tears after evaluation and authorization of the investigator. Dosage and time were noted in the Diary. As the use of other eye drops or medications for eye topical use in addition to artificial tears may affect the eye discomfort (OSDI) score and the overall clinical picture, this possibility is in itself a negative factor for the judgement of efficacy and tolerability of treatment. The possibility of events and adverse effects of mild, moderate or severe intensity had to be reported in CRF along with the date and time of occurrence, date and time of disappearance, duration. The intensity, the relationship to treatment, the actions taken and administered therapies must be reported as well.

Collected data were analysed using descriptive techniques and inferential statistics in order to highlight any differences between the baseline condition and that ascertained at the end of the application of the treatment with the device according to the invention called Rexon Eye.

The categorical variables (gender, events and adverse effects, . . . ) were analysed descriptively reporting the number and percentage of subjects in each category. For the quantitative variables (such as age) the mean and the standard deviation have been reported in the case of normal distribution, while the median, the minimum and the maximum were reported in the opposite case.

The change between baseline and end of the quantitative variables (number of drops of tear substitutes, OSDI score, results of lacrimal function tests, osmolarity of the tear, visual acuity) was analysed using the Student t test for dependent samples or the Wilcoxon signed rank test. The change between baseline and end of categorical variables (descriptors of the clinical condition, results of the evaluation to the slit lamp, . . . ) was analysed with the McNemar test in the case of two categories or with the Bowker test in the case of more than two categories. The variation between baseline and the quantitative variables final was also compared with the inherent variability of the variables, expressed by the standard deviation of the values of the controls at visit 0 and 1 visit. All tests were two-tailed with a significance level of 5%. The result of the statistical tests is accompanied by a confidence interval of 95% for an average or a median, or a proportion. The study was conducted according to the principles of Good Clinical Practice (ICH Harmonized Tripartite Guidelines for Good Clinical Practice in 1996 Directive 91/507/EEC; DM 15 Jul. 1997), the Declaration of Helsinki and the national regulations regarding the conduct of clinical trials. The following are the results of the clinical trial: Table 2 summarizes the demographic data of the 27 test persons:

TABLE 2

| | Number | % |
|---|---|---|
| Gender | | |
| Male | 6 | 22 |
| Female | 21 | 78 |
| Origin | | |
| Asian | 0 | 0 |
| Black | 1 | 4 |
| Caucasian | 26 | 96 |
| other | 0 | 0 |
| Systemic risk for DTS | | |

TABLE 2-continued

|  | Number | % |
|---|---|---|
| No | 19 | 70 |
| Yes | 8 | 30 |
| RA (Rheumatoid Arthritis) | 2 | — |
| Sjögren | 4 | — |
| Other | 2 | — |
| MGD (dysfunction of the meibomian glands) | | |
| Yes | 7 | 26 |
| No | 20 | 74 |
| Age (years) | | |
| Range | 23-82 | |
| Mean (SD) | 57 (15) | |
| median | 58 | |
| Duration of DTS (years) | | |
| Range | 1-55 | |
| Mean (SD) | 11.8 (13.4) | |
| median | 10 | |

The visits from 0 to 12 will be referred to as V0, V1, . . . , V12. V0 represents the first baseline, V1 represents the second baseline, V2 is the first treatment, V8 is the visit a month after the first treatment, V12 is the visit 2 months after the first treatment and the last treatment, V13 represents the visit one week after the last treatment and visits V14 and V15 represent, respectively, the visit 6 months after the last treatment and 18 months after the last treatment. Among the 27 tested, 18 people have a hyper-evaporation and 11 have a hypo-secretion, two people thus show both phenomena.

Table 3 summarizes the results of the OSDI questionnaire highlighting the frequency of dry eye symptoms in specific contexts, such as with the use of a computer, while driving a car, during the week prior to the study. Normal values are values in the range from 0 to 13, slight values are values from 13 to 23, moderate values are values from 23 to 33 and serious values are values from 33 to 100.

TABLE 3

|  |  | Baseline | | V8 | | V13 | | V14 | | V15 | |
|---|---|---|---|---|---|---|---|---|---|---|---|
|  |  | N | % | N | % | N | % | N | % | N | % |
| All | normal | 0 | 0 | 7 | 26 | 9 | 33 | 7 | 27 | 7 | 28 |
|  | slight | 3 | 11 | 7 | 26 | 5 | 19 | 9 | 35 | 8 | 32 |
|  | moderate | 6 | 22 | 4 | 15 | 4 | 15 | 3 | 11 | 2 | 8 |
|  | severe | 18 | 67 | 9 | 33 | 9 | 33 | 7 | 27 | 8 | 32 |
|  | n.r. |  |  |  |  |  |  | 1 |  | 2 |  |
| Hyper-evapo-ration | normal | 0 | 0 | 6 | 33 | 6 | 33 | 6 | 33 | 3 | 18 |
|  | slight | 3 | 17 | 3 | 17 | 3 | 17 | 4 | 22 | 7 | 41 |
|  | moderate | 4 | 22 | 4 | 22 | 4 | 22 | 3 | 17 | 1 | 6 |
|  | severe | 11 | 61 | 5 | 28 | 5 | 28 | 5 | 28 | 6 | 35 |
|  | n.r. |  |  |  |  |  |  |  |  | 1 |  |
| Hypo-secre-tion | normal | 0 | 0 | 1 | 10 | 5 | 45 | 2 | 20 | 4 | 40 |
|  | slight | 0 | 0 | 4 | 36 | 2 | 19 | 5 | 50 | 2 | 20 |
|  | moderate | 3 | 27 | 1 | 10 | 2 | 18 | 1 | 10 | 1 | 10 |
|  | severe | 8 | 73 | 5 | 44 | 2 | 18 | 2 | 20 | 3 | 20 |
|  | n.r. |  |  |  |  |  |  | 1 |  | 1 |  |

N = number;
n.r. = not registered

Figure 2:
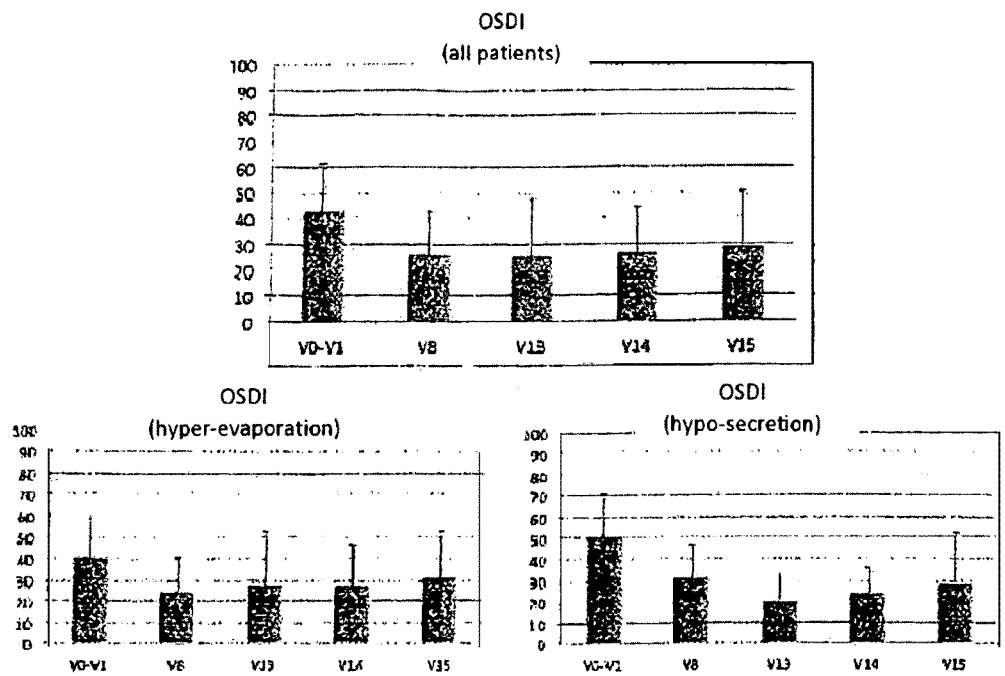
FIG. 2 shows the results of clinical trials on the application of the device and method according to the invention in terms of OSDI values (mean and SD) with different examinations for all patients (top), for patients with hyper-evaporation (bottom left) and for patients with hypo-secretion (lower right)

FIG. 2 shows these results of clinical trials of Table 3 on the application of the device and method according to the invention in terms of OSDI values (mean and SD) with different examinations for all patients (top), for patients with hyper-evaporation (bottom left) and for patients with hypo-secretion (lower right) in bar diagrams.

A remarkable improvement in the symptoms is highlighted for a large number of patients, as well as a duration in time of the positive effect of the treatment.

Table 4 summarizes the test results for the stability of the tear film. In the TBUT (tear break-up time) test, the time was measured with a stopwatch and an average of three readings was used for data analysis. The longer the time, the more stable the tear film. A break-up time for the tear film is a sign of a poor tear film and represents a great probability of a dry eye. TBUT values are divided into the following classes: ≤10 s=normal; 10-5 s=at the limit; and <5 s=low.

TABLE 4

|  |  | Baseline | | V13 | | V14 | | V15 | |
|---|---|---|---|---|---|---|---|---|---|
|  |  | N | % | N | % | N | % | N | % |
| All | normal | 0 | 0 | 6 | 22 | 3 | 12 | 4 | 17 |
|  | limit | 12 | 44 | 11 | 41 | 13 | 50 | 13 | 57 |
|  | low | 15 | 56 | 10 | 37 | 10 | 38 | 6 | 26 |
|  | n.r. |  |  |  |  | 1 |  | 4 |  |
| Hyper-evaporation | normal | 0 | 0 | 5 | 28 | 1 | 6 | 2 | 13 |
|  | limit | 9 | 50 | 8 | 44 | 11 | 61 | 11 | 69 |
|  | low | 9 | 50 | 5 | 28 | 6 | 33 | 3 | 18 |
|  | n.r. |  |  |  |  |  |  | 2 |  |
| Hypo-secretion | normal | 0 | 0 | 1 | 9 | 2 | 20 | 1 | 12 |
|  | limit | 3 | 27 | 3 | 27 | 3 | 30 | 4 | 44 |
|  | low | 8 | 73 | 7 | 64 | 5 | 50 | 4 | 44 |
|  | n.r. |  |  |  |  | 1 |  | 2 |  |

N = number;
n.r. = not registered

Figure 3:
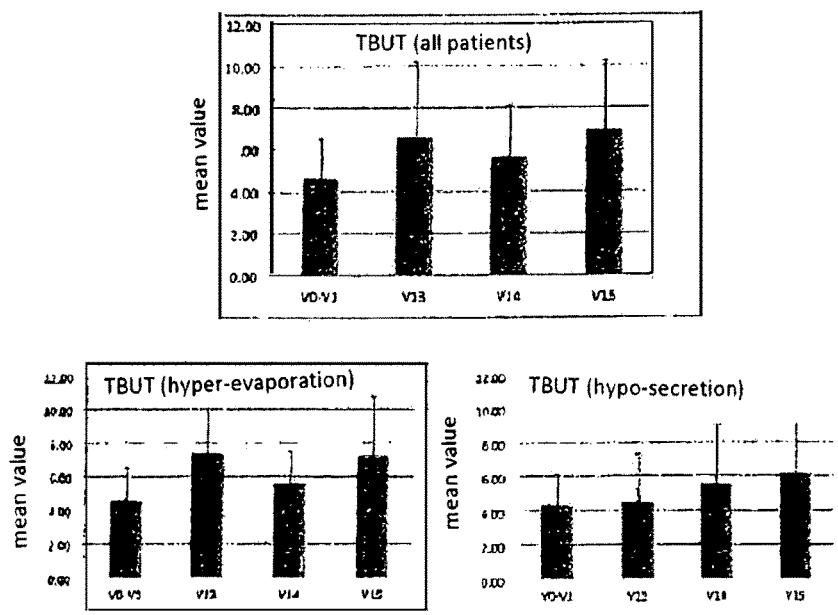
FIG. 3 shows the TBUT values (mean and SD) for different examinations for all patients (top), for patients with hyper-evaporation (bottom left) and for patients with hypo-secretion (lower right)

FIG. 3 shows the TBUT values (mean and SD) of Table 4 for different examinations for all patients (top), for patients with hyper-evaporation (bottom left) and for patients with hypo-secretion (lower right). A remarkable improvement in the symptoms is highlighted for a large number of patients, as well as a duration in time of the positive effect of the treatment. The improving effect seems to occur more sharply after a long time since the last treatment. For the evaluation of the degree of corneal staining, the Oxford scheme (FIG. 1) was used. The surface damage of the exposed eye is ranked against standard values. Spots are represented by dots on a series of tables and values range from 0-5, with 0 being the best condition. Table 5 summarizes the results.

TABLE 5

|  |  | Baseline | | V13 | | V14 | | V15 | |
|---|---|---|---|---|---|---|---|---|---|
|  |  | N | % | N | % | N | % | N | % |
| All | 0 | 2 | 7 | 19 | 70 | 22 | 85 | 14 | 61 |
|  | 1 | 17 | 63 | 5 | 18 | 3 | 12 | 6 | 26 |
|  | 2 | 6 | 22 | 1 | 4 | 1 | 3 | 2 | 9 |
|  | 3 | 1 | 4 | 0 |  | 0 |  | 0 |  |
|  | 4 | 1 | 4 | 1 | 4 | 0 |  | 1 | 4 |
|  | 5 | 0 |  | 0 |  | 0 |  | 0 |  |
| Hyper-evaporation | 0 | 1 | 6 | 15 | 88 | 15 | 83 | 9 | 56 |
|  | 1 | 12 | 66 | 1 | 6 | 2 | 11 | 4 | 25 |
|  | 2 | 4 | 22 | 1 | 6 | 1 | 6 | 2 | 13 |
|  | 3 | 1 | 6 | 0 |  | 0 |  | 0 |  |
| Table 5 (cont.) | 4 | 0 |  | 0 |  | 0 |  | 1 | 6 |
|  | 5 | 0 |  | 0 |  | 0 |  | 0 |  |
| Hypo-secretion | 0 | 1 | 9 | 6 | 55 | 9 | 90 | 5 | 56 |
|  | 1 | 6 | 55 | 4 | 36 | 1 | 10 | 2 | 22 |
|  | 2 | 3 | 27 | 0 |  | 0 |  | 2 | 22 |
|  | 3 | 0 |  | 0 |  | 0 |  |  |  |
|  | 4 | 1 | 9 | 1 | 9 | 0 |  |  |  |
|  | 5 | 0 |  | 0 |  | 0 |  |  |  |

N = number

Figure 4:
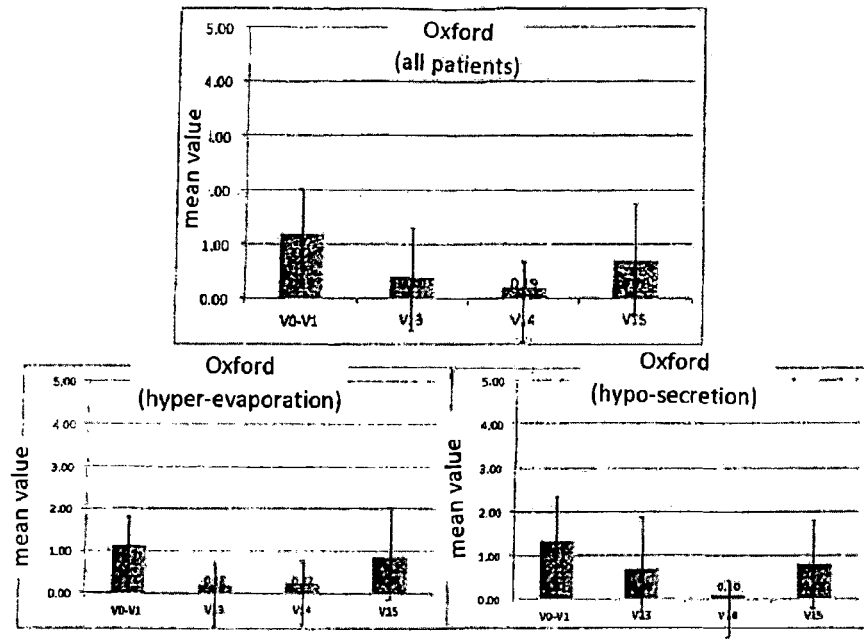
FIG. 4 shows the values for the Oxford corneal stains (average and SD) for different examinations for all patients (top), for patients with hyper-evaporation (bottom left) and for patients with hypo-secretion (lower right)

FIG. 4 shows the corneal stain values (mean and SD) of Table 5 for different examinations for all patients (top), for patients with hyper-evaporation (bottom left) and for patients with hypo-secretion (lower right) in bar diagrams.

A remarkable improvement in the symptoms is highlighted for a large number of patients, as well as a duration in time of the positive effect of the treatment.

In conclusion of test results, Table 6 below reports the results of the Schirmer test in which strips of paper are placed in the eye for a few minutes to measure the production of tears. The test values are expressed as the length of wet paper. Normal values correspond to lengths of ≤15 mm, values for minor pathologies correspond to lengths from 14 to 9 mm, values for moderate pathologies correspond to length from 8 to 4 mm, and values less than 4 mm correspond to serious pathologies.

TABLE 6

|  |  | Baseline | | V13 | | V14 | | V15 | |
|---|---|---|---|---|---|---|---|---|---|
|  |  | N | % | N | % | N | % | N | % |
| All | normal | 0 | 0 | 6 | 22 | 3 | 12 | 7 | 31 |
|  | slight | 7 | 26 | 10 | 37 | 9 | 35 | 7 | 31 |
|  | moderate | 14 | 52 | 5 | 19 | 8 | 31 | 5 | 22 |
|  | severe | 6 | 22 | 6 | 22 | 6 | 22 | 4 | 16 |
|  | n.r. |  |  |  |  | 1 |  | 4 |  |
| Hyper-evaporation | normal | 0 | 0 | 6 | 33 | 1 | 6 | 6 | 38 |
|  | slight | 7 | 39 | 6 | 33 | 7 | 39 | 5 | 31 |
|  | moderate | 8 | 44 | 4 | 22 | 7 | 39 | 4 | 25 |
|  | severe | 3 | 17 | 2 | 12 | 3 | 16 | 1 | 6 |
|  | n.r. |  |  |  |  |  |  | 2 |  |
| Hypo-secretion | normal | 0 | 0 | 1 | 10 | 2 | 20 | 1 | 12 |
|  | slight | 1 | 10 | 4 | 36 | 3 | 30 | 3 | 33 |
|  | moderate | 7 | 63 | 1 | 10 | 2 | 20 | 2 | 22 |
|  | severe | 3 | 27 | 5 | 44 | 3 | 30 | 3 | 33 |
|  | n.r. |  |  |  |  | 1 |  | 2 |  |

N = number;
n.r. = not registered

Figure 5:
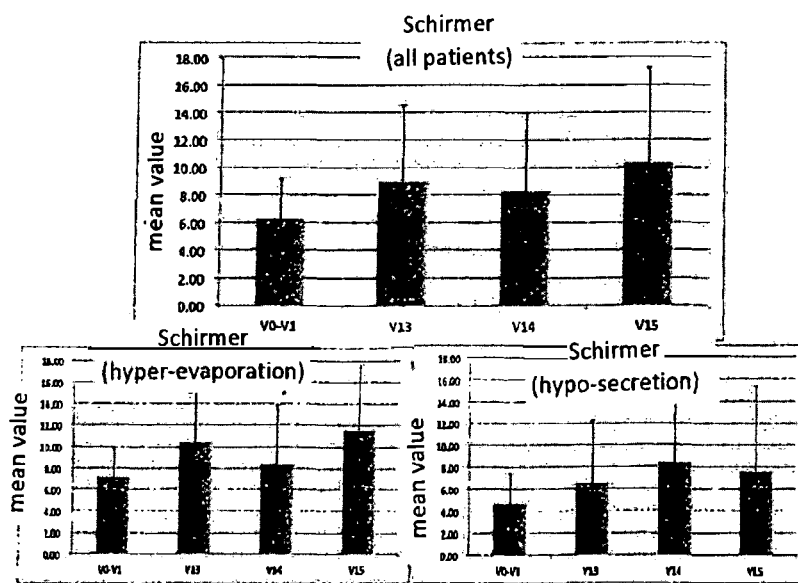
FIG. 5 shows the values for the Schirmer test results (average and SD) for different examinations for all patients (top), for patients with hyper-evaporation (bottom left) and for patients with hypo-secretion (lower right)

FIG. 5 shows the values of the results of the Schirmer test (mean and SD) of Table 6 for different examinations for all patients (upper), for patients with hyper-evaporation (bottom left) and for patients with hypo-secretion (lower right) in bar diagrams.

A remarkable improvement in the symptoms is highlighted for a large number of patients, as well as a duration in time of the positive effect of the treatment. The improving effect seems to occur more sharply after a long time since the last treatment.

The test results show that the invention has achieved the object to eliminate dry eye symptoms, and in some cases probably also the origin of dry eye, and at least increase the frequency necessary for dry eye treatments in most patients.

Below, an executive example will be described for an electrode system according to the invention with reference to FIGS. 6 to 10. The presented electrode is suitable for the stimulation of the eyelid area using electromagnetic fields at high frequencies. A system of electrodes suitable for the stimulation of the eye by means of electromagnetic fields at high frequencies (4 MHz resonance frequency, harmonics up to 64 MHz) and compatible with the device according to the invention is described.

Figure 6:
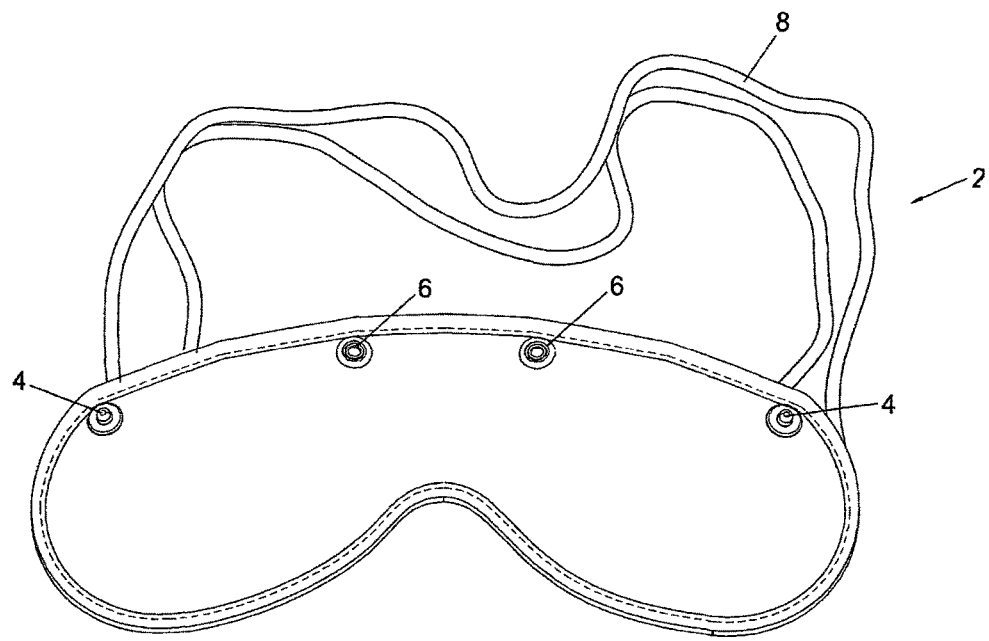
FIG. 6 shows a perspective view of a mask-shaped electrode system according to the invention.

FIG. 6 shows the general structure of an electrode system in the form of mask 2 viewed from the outside. The mask 2 has two female button connectors 4 for the direct connection of two electrodes (which are located inside the mask) to the device according to the invention by means of standard connectors. Then, through clips 6 are identified for positioning a thermocouple contactable by means of an adapter to a thermal detection card of the device or of a possible temperature sensor inserted into the connector connected to the machine via an adapter to a thermal detection card of the device. The mask 2 may be made of polyester with elastic bands 8 to fix the mask on the head. In the specific case represented, the handpiece has a face-side cotton finishing.

Figure 7:
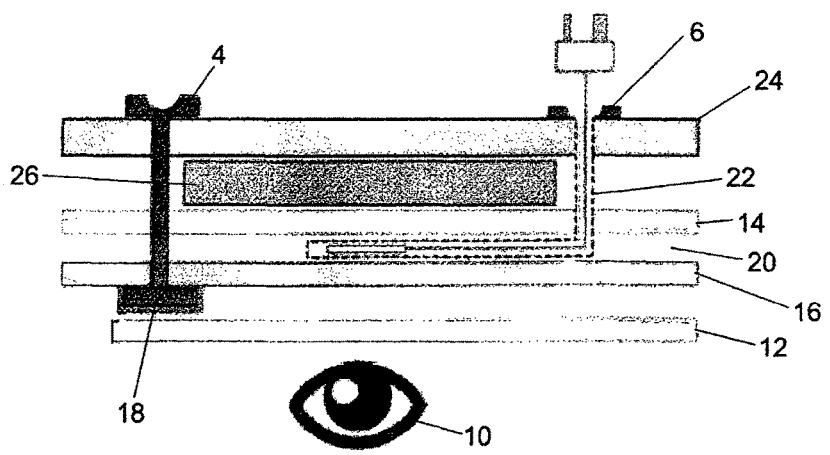
FIG. 7 shows the section of the mask of FIG. 6 in a schematic sketch.

FIG. 7 shows the internal structure of the handpiece in a schematic sketch in section. A cotton layer 12 is in contact with the eye 10. This cotton layer 12 includes, along with a second cotton layer 14, an electrode 16 layer. Between the first cotton layer 12 and the electrode 16 an insulator 18 is inserted for insulating the internal contacts, and between the second cotton layer 14 and the electrode 16, in an interstitial space 20, a thermocouple 22 is inserted. The interstitial space 20 thus serves for the insertion and positioning of the temperature probe 22, isolated from the electrode 16, positioned in the vicinity of the eyelid to be able to detect the local temperature. The electrode 16 is realized by means of different technologies (as described above) and integrated in proximity of the cotton layer 12 in contact with the eyelid. Above the second cotton layer 14 and the outer mask 24 there are gel pockets 26 positioned at eye level to increase adhesion of the electrodes 16 to the eyelid.

Figure 8:
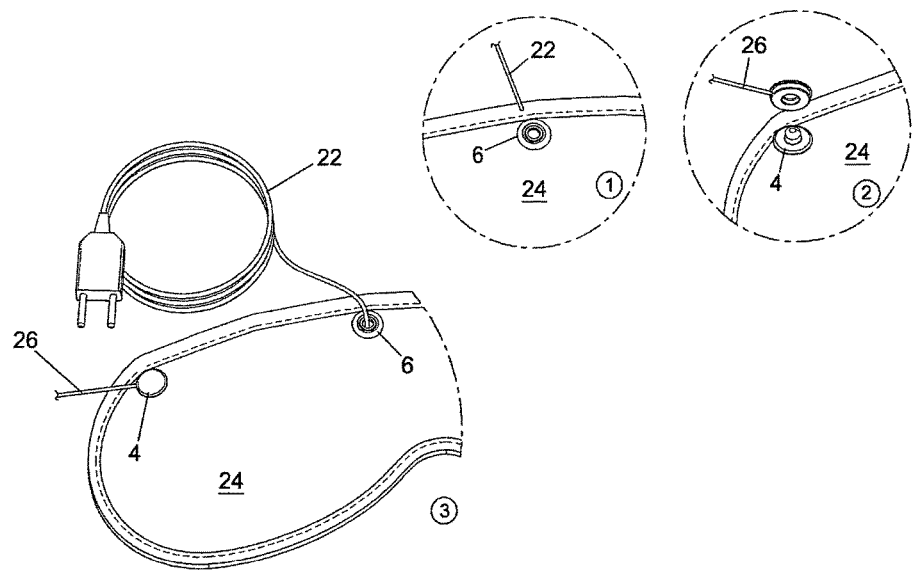
FIG. 8 shows the connection assembly phases for the use of the mask of FIGS. 6 and 7.
Figure 9:
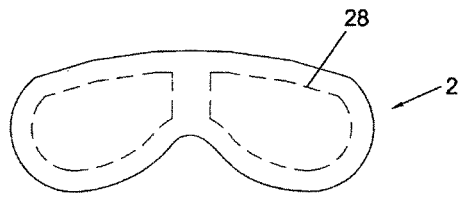
FIG. 9 shows the extension and positioning of the electrodes inside the mask according to FIGS. 6 to 8.
Figure 10:
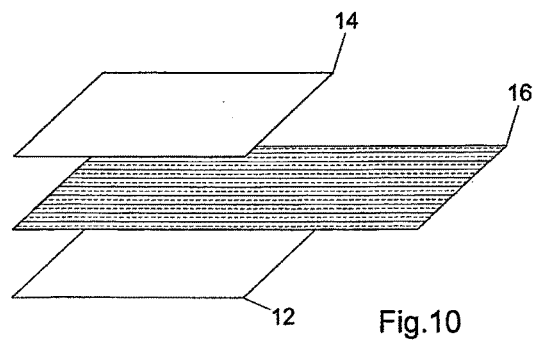
FIG. 10 shows a detail of the mask according to FIGS. 6 to 9.

FIG. 8 shows the assembly of the handpiece connections. In phase 1, the probe of the thermocouple 22 is inserted by about 2 cm inside the housing so as to obtain the detection of the temperature at a point as close as possible to the eyelid. In phase 2, for fastening of electrical connections 26, the connector button is completely depressed and correct connection is checked by turning the connector. In the third step, once the thermal probe 22 is positioned and the button connector is connected, it is possible to connect the handpiece to the device according to the invention. FIG. 9 shows in dashed lines 28 the extension and the positioning of the layer of electrodes inside the handpiece of mask 2. FIG. 10 shows the sandwich structure between two protective layers 12 and 14, of flexible mask fabric (that generalize the use of cotton) and the electrode 16 in the middle that in this specific case is a fabric with short-circuited aluminum texture.

Another fabric suitable as an electrode is a highly-deformable, thick-weft fabric with a silver (92%) wire and Nylon Dorlastan® (8%) that gives the material a high elasticity. The advantages of this material are high conductivity, high deformability that allows adhesion and adaptation to uneven surfaces, a wide range of temperatures from −30 to 90° C. and a 100% deformability in the horizontal direction and 65% in the vertical direction. The thickness of the silver wire should be chosen so as to withstand high powers. Even if the fabric just described appears to be an optimum material as it is adaptable to surfaces thanks to the materials that compose it, the material can be replaced by materials such as, for example, the ones described above as long as they are adaptable to uneven surfaces.

The electrode system in the shape of a mask may of course also be an electrode system in the form of goggles (e.g. like ski goggles) containing inside the active part described above. A goggle-shaped electrode system is described below with reference to FIGS. 11 to 26 which represent in various views an electrode system according to the invention.

Figure 11:
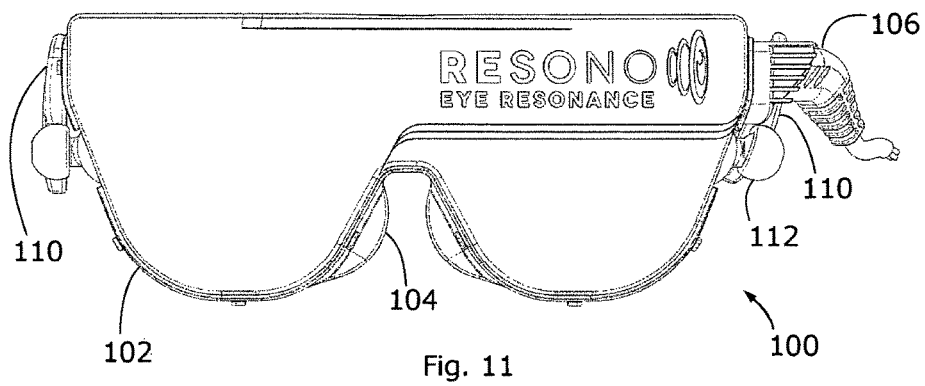
FIG. 11 shows a front view of a further example for a goggle-shaped electrode system according to the invention.

FIG. 11 shows this further example for an electrode system according to the invention in the form of goggles in a front view. Goggles are generally referred to with 100. It is noted that the outer rigid shell 102 of goggles 100 has two lugs 104. On the right there is an electrical and data connection 106, which is derived from a device that generates electromagnetic waves, such as a RexonAge device by Telea Electronic Engineering Srl, based in Sandrigo (Italy).

Figure 12:
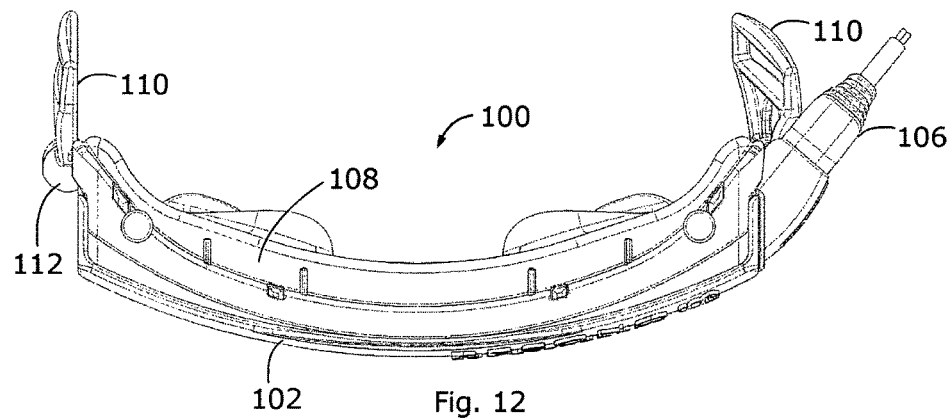
FIG. 12 shows the electrode system of FIG. 11 in a top view.

In FIG. 12 we see the same goggles 100 from above. Note the outer shell 102 as well as a rubber cover 108 that forms the inner part (facing towards the patient) of goggles 100, which is fixed on the outer shell 102. On the sides there are two articulated joints 110 (articulations 112) with respect to the central body of goggles, suitable to receive, for instance, the ends of a strap for securing the goggles on the head. In the rear view of FIG. 13, the inside rubber cover 108 which mimics the anatomy of the area of the patient's eyes is clearly visible. FIG. 14 shows the electrode system of FIG. 1 in two side views; the side with the electrical and data connection 106 and the side with no connection are shown on the left and on the right, respectively. It is possible to see clearly, as also for example in FIG. 14, the articulation 112 of the strap (not represented) joint in the form of a ball joint. The semi-frontal perspective view of FIG. 15 and the perspective view of FIG. 16 from the back are further illustrations to show the three-dimensional configuration of goggles.

Figure 13:
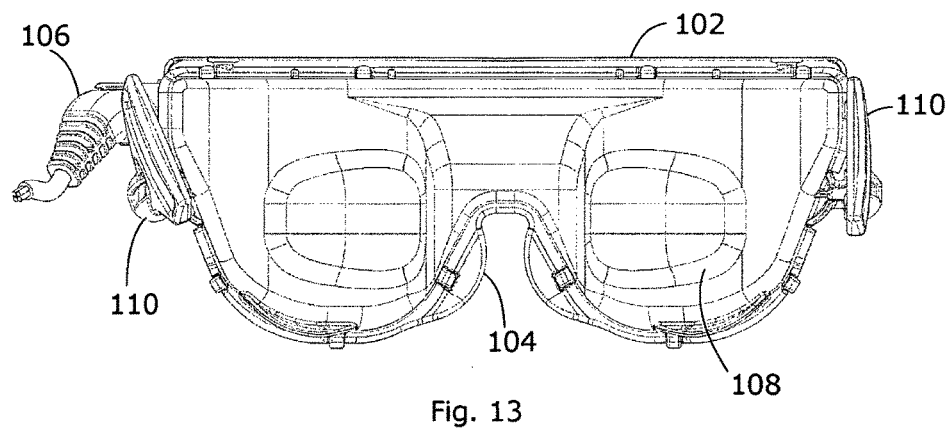
FIG. 13 shows the electrode system of FIG. 11 in a rear view.
Figure 17:
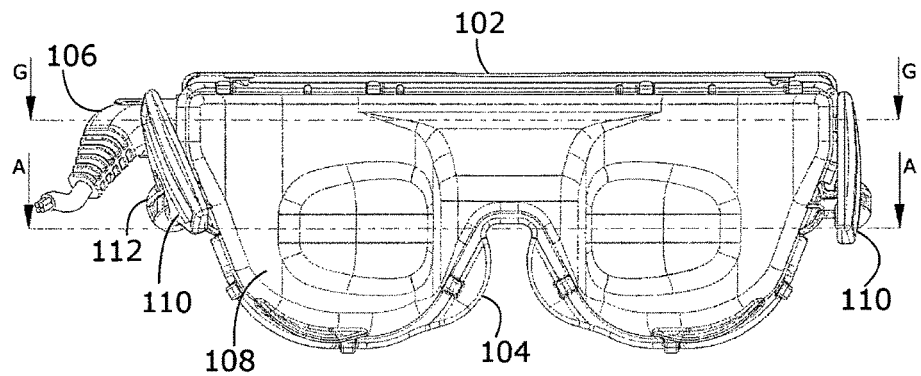
FIG. 17 corresponds to FIG. 13 indicating the position of sections G-G and A-A represented by FIGS. 20 and 18, respectively.
Figure 18:
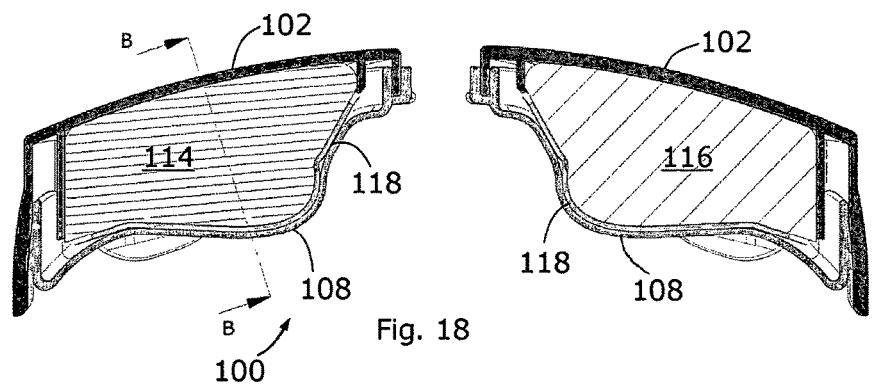
FIG. 18 shows the section A-A according to FIG. 17.
Figure 19:
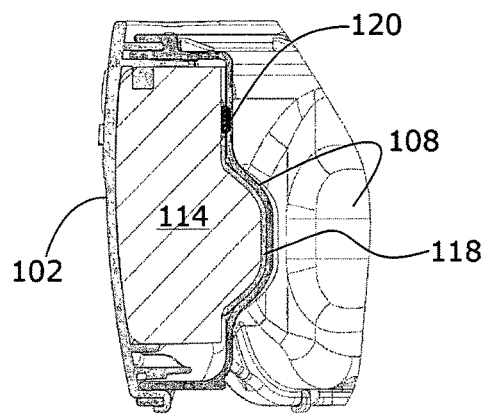
FIG. 19 shows the section B-B according to FIG. 18.

FIG. 17 corresponds to FIG. 13 and indicates the position of sections G-G and A-A, which are then represented respectively in FIGS. 20 and 18. The section A-A of FIG. 18 illustrates the sandwich configuration of goggles 100. The outer shell 102 is followed by a damping cushion 114, 116 respectively for the left eye and the right eye, a conductive and radiating fabric 118 and finally by the rubber cover 108 which closes the glasses towards the inside. The same layering is evident from the section B-B shown in FIG. 19 in which one can note the presence of a temperature probe 108 to control a possible excessive heating of glasses in the vicinity of the area that will be in contact with a part of the eye area of the head.

In the section of FIG. 20 (corresponding to the section G-G shown in FIG. 17), details of the electrical and data connection 106 can be observed, still better visible in the enlarged detail of FIG. 21. A cable 122 (outgoing from the device—not represented—that provides the specific electromagnetic waves foreseen by the invention) terminates in a fitting 124 having inner channel-shaped openings to comprise a pair of connections 126 for power transfer, that is for radiofrequency waves, and a pair of data transfer connections 128 that connect to the respective electrical and data circuits applied on a film, i.e. a thin electronic card (visible in FIG. 23) in which conductive and radiating fabric (visible in FIG. 23) will be inserted and fixed as a window with a conductive double-sided adhesive. The fitting 124 of the connection or electrical connector 106 is inserted into a corresponding socket 130 which is interlockingly inserted on a side part of the outer shell 102 of the goggles. FIG. 22, showing the section L-L indicated in FIG. 20, shows how the rubber cover 108 lodges in crevices created in the interior parts of the outer shell 102 of the goggles and how the damping cushion 114 is housed in shapings of the outer shell 108.

Figure 23:
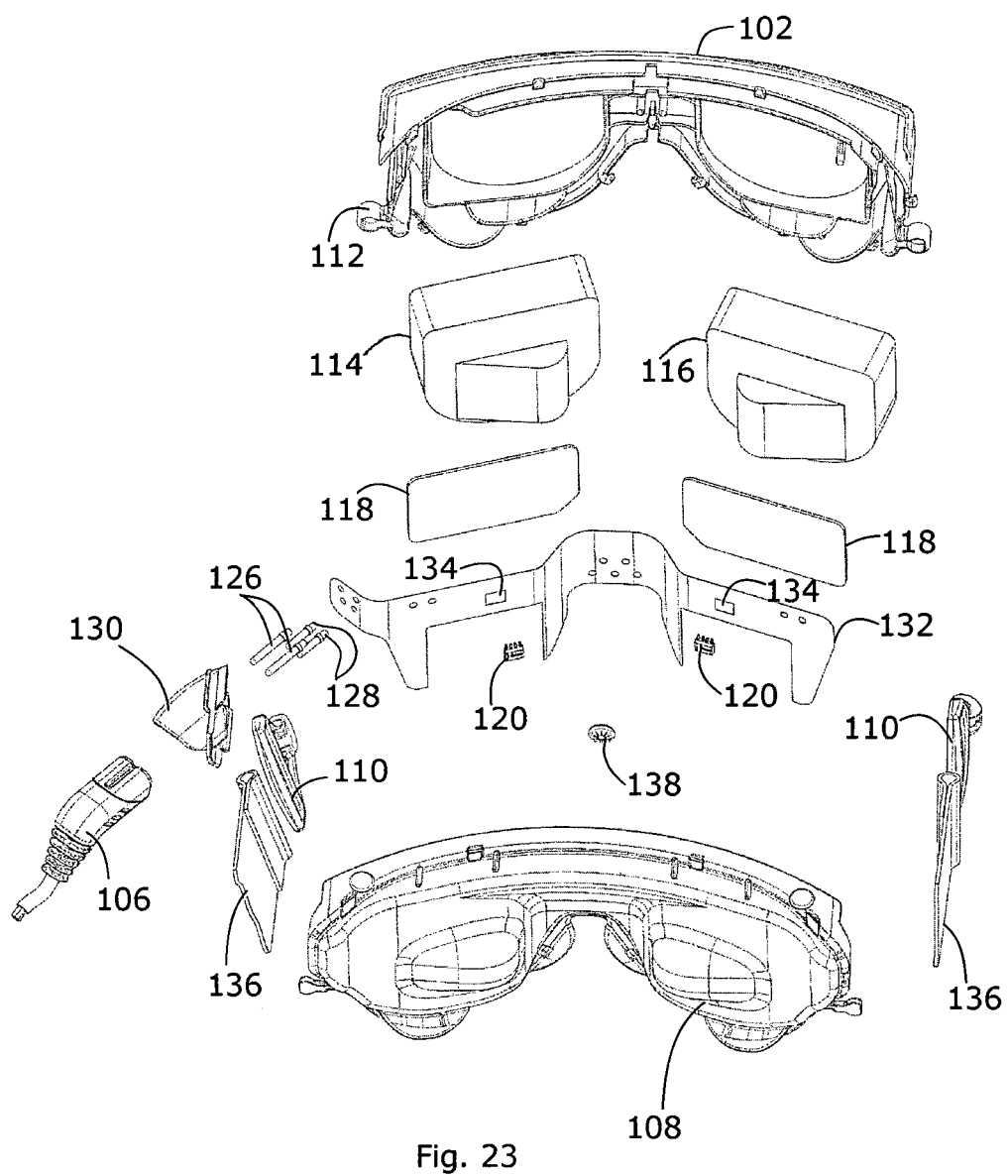
FIG. 23 shows the electrode system of FIG. 11 in an exploded view.

FIG. 23 shows the electrode system of FIG. 11 in an exploded view and illustrates the individual components of the goggles that are then assembled to form the goggles. At the top there is the outer shell 102 in which the two damping cushions 114 and 116 will be inserted, with a geometrical shape such as to deform the conductive and radiating fabric 118 and the rubber cover 108 so as to mimic the shape of the eye or of parts of the head that surround it. Two sheets of conductive and radiating fabric 118 are inserted into openings as windows in the film 132 and fixed with a conductive double-sided adhesive (not shown) on this. The film 132 includes the electrical circuit and the data circuit (for the transfer of control data, such as temperature, or impedance values) and includes two seats 134 for thermal probes 120. Connections 126 and 128 are shown. The outer shell 102 has on both sides joints 112 to connect to connections 110 on which the ends 136 of a strap (not fully shown) will be fixed.

Figure 24:
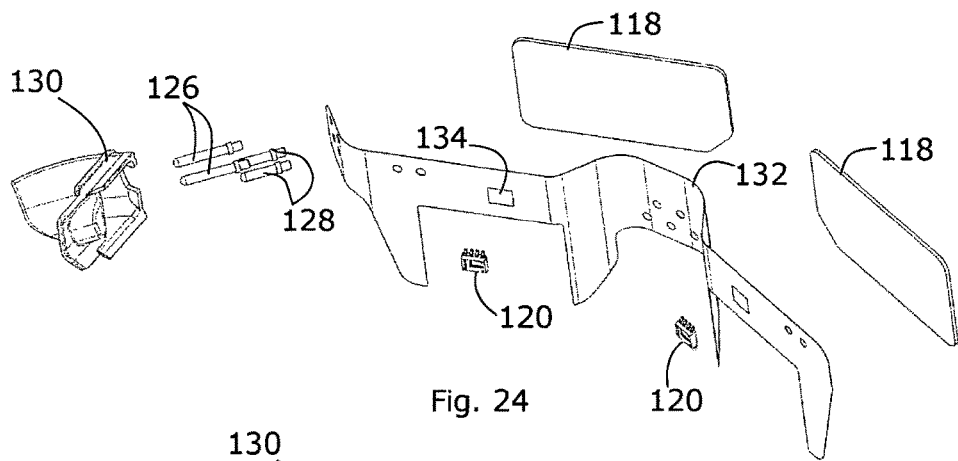
FIG. 24 shows a detail of FIG. 23 in an exploded perspective view.
Figure 25:
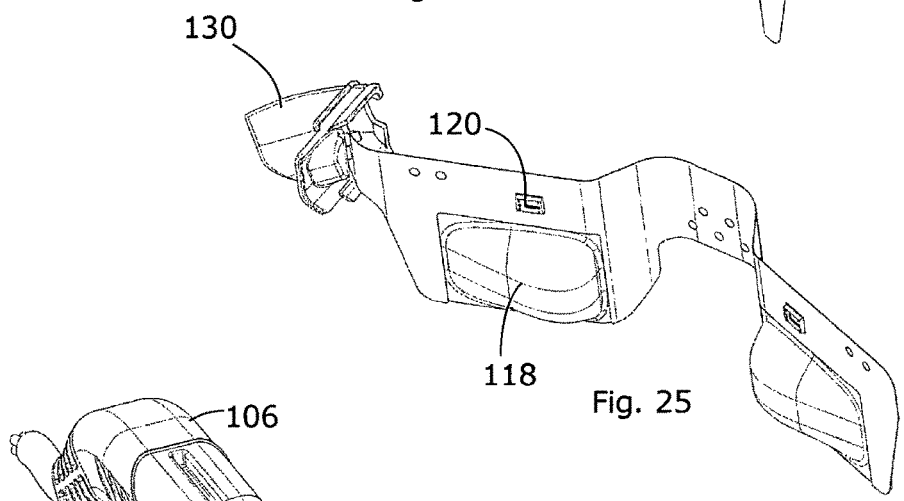
FIG. 25 shows the detail of FIG. 24 in the assembled state, indicating the deformation of the conductive part of the electrode.
Figure 26:
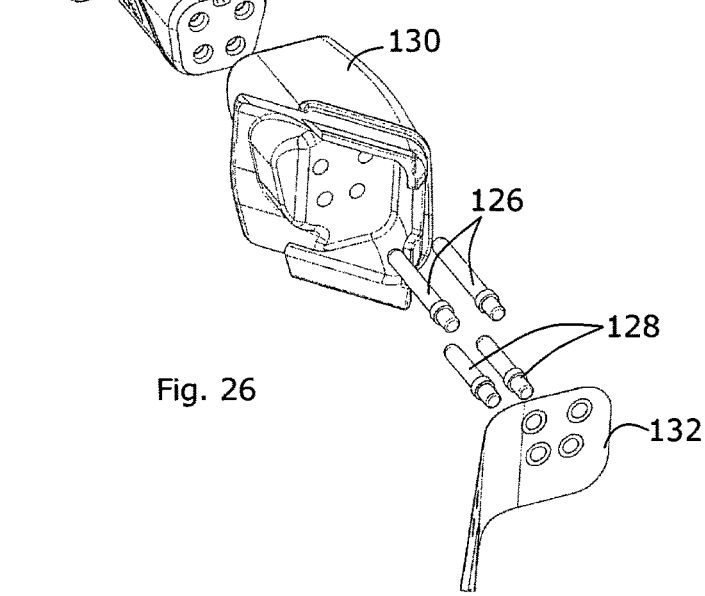
FIG. 26 shows the electrical and data connection of goggles according to FIG. 11 in an exploded view.

FIG. 24 shows a detail of FIG. 23 in an exploded perspective view, while FIG. 25 shows the detail of FIG. 24 in assembled state indicating the deformation of the conductive part of the electrode, that is, the conductive and radiating fabric 118. The film 132 has four holes on the left to insert connections 126 and 128. FIG. 26 shows the electrical and data connection between the device that provides the electromagnetic waves (and includes a controller for processing data from goggles or to transmit signals) and the goggles according to FIG. 11 in an exploded view.

REFERENCES

[1] Lemp M A. Report of the National Eye Institute/Industry workshop on clinical trials in Dry Eyes. CLAO J. 1995; 21:221-232;
[2] Report of the International Dry Eye WorkShop (DEWS), Ocul Surf. 2007; 5(2):69-204;
[3] Dal Maschio M et al. Biophysical effects of high frequency Electrical field (4-64 MHz) on muscle fibers in culture. Basic Applied Myology. 2009; 19 (1):49-56;
[4] B. Kronemyer. Resonax emits high frequency currents to stimulate tissues. Aesthetic Buyers Guide. September/October 2006. www.miinews.com.
[5] Schiffman R M et al. Reliability and validity of the eye Surface Index. Arch Ophthalmol. 2000; 118:615-621.
[6] Suzuki M et al. Tear osmolarity as biomarker for dry eye disease severity. Invest Ophthalmol Vis Sci. 2010; 51:4557-4561.

During implementation, the electrode system, the device, the method and the use object of the invention may undergo further embodiment modifications or variants, not described herein. If such modifications or such variants should fall within the scope of the following claims, they should all be considered protected by the present patent.

The invention claimed is:

1. An electrostimulation device for treating dry eye, comprising:
   (i) an electrode system comprising one or more electrodes wherein (a) a portion of said one or more electrodes intended to be applied in contact with the eye, the eye orbit, the temple, the eyelid areas or a part of them, respectively imitates the surface shape of the eye, the eye orbit, the temple, the eyelid areas or a part of them or wherein (b) a portion of said one or more electrodes intended to be applied in contact with the eye, the eye orbit, the temple, the eyelid areas or a part of them is flexible and adaptable in its shape in such a way that in the cases (a) and (b) a form-fit coupling is achievable between said portion of said one or more electrodes and the surface shape of the eye, the eye orbit, the temple, the eyelid areas or a part of them, wherein said portion of said one or more electrodes intended to be applied in contact with the eye, the eye orbit, the temple, the eyelid areas or a part of them is fed or feedable with an electromagnetic wave of distorted sinusoidal current with a resonance frequency, which includes the related harmonics; and
   (ii) a radiofrequency circuit suitable to emit an electromagnetic wave of distorted sinusoidal current with a resonance frequency which includes the related harmonics, in which the electromagnetic wave of distorted sinusoidal current feeds said one or more electrodes, and in particular said portion of said one or more electrodes intended to be applied in contact with the eye, the eye orbit, the temple, the eyelid areas or a part of them, wherein said portion of said one or more electrodes extends to cover the eye, the eye orbit and the eyelid areas of the eye, wherein said portion in its extension involves most of the meibomian glands and of the lacrimal glands.

2. The electrostimulation device according to claim 1, wherein said portion of said one or more electrodes is flexible and adaptable in its shape and in that said portion comprises as a conductive and radiating element a metallic fabric which presents different extensibility in the two dimensions that define its superficial extension.

3. The electrostimulation device according to claim 1, wherein said portion of said one or more electrodes is flexible and adaptable in its shape and in that said portion comprises on the side intended to come in contact with the patient an insulation layer suitable to allow only the passage of frequencies greater than 100 kHz.

4. The electrostimulation device according to claim 1, wherein said portion of said one or more electrodes is flexible and adaptable in its shape and in that said portion comprises, in a sandwich structure, in the following order, a damping cushion, a conductive and radiating element and an insulation layer in which said conductive and radiating element is integrated as a window in an opening of a film that carries an electric circuit for feeding said conductive and radiating element with electromagnetic waves and which is part of the electrode and in which the damping cushion, the conductive and radiating element, the insulation layer and the film with the circuit are all flexible and adaptable in their shape to the area of the eye, the eye orbit, the temple, the eyelid areas or a part of them.

5. The electrostimulation device according to claim 1, wherein it comprises an electrical circuit for the transmission of electromagnetic waves configured such that said electrical circuit is open and that it is only closable by an external object, as the load impedance to which electromagnetic waves are transmitted.

6. The electrostimulation device according to claim 1, wherein the resonance frequency is 4 MHz.

7. The electrostimulation device according to claim 1, wherein the related harmonics include at least the second and third harmonic.

* * * * *

UNITED STATES PATENT AND TRADEMARK OFFICE
CERTIFICATE OF CORRECTION

PATENT NO. : 10,376,691 B2
APPLICATION NO. : 15/540721
DATED : August 13, 2019
INVENTOR(S) : De Toni et al.

It is certified that error appears in the above-identified patent and that said Letters Patent is hereby corrected as shown below:

On the Title Page

(73) Assignee should read:
RESONO OPHTHALMIC S.R.L.,
Trieste (TS) (IT)

Signed and Sealed this
Fourteenth Day of July, 2020

Andrei Iancu
*Director of the United States Patent and Trademark Office*